United States Patent
Chen et al.

(10) Patent No.: US 7,505,866 B2
(45) Date of Patent: Mar. 17, 2009

(54) METHOD OF CLASSIFYING DATA USING SHALLOW FEATURE SELECTION

(75) Inventors: Xuewen Chen, Lawrence, KS (US); Jiangsheng Yu, Beijing (CN)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 11/750,482

(22) Filed: May 18, 2007

(65) Prior Publication Data

US 2007/0271075 A1      Nov. 22, 2007

Related U.S. Application Data

(60) Provisional application No. 60/802,365, filed on May 22, 2006.

(51) Int. Cl.
*G06F 17/18* (2006.01)
(52) U.S. Cl. .................................................. 702/181
(58) Field of Classification Search .................. 702/181
See application file for complete search history.

(56) References Cited

U.S. PATENT DOCUMENTS

| | | | |
|---|---|---|---|
| 7,194,380 B2 * | 3/2007 | Barrow et al. ................ 702/181 |
| 2002/0111742 A1 * | 8/2002 | Rocke et al. .................. 702/19 |
| 2004/0043436 A1 * | 3/2004 | Vlahou et al. .............. 435/7.23 |
| 2005/0273269 A1 * | 12/2005 | Yakhini et al. ................ 702/19 |
| 2006/0035250 A1 * | 2/2006 | Natsoulis ....................... 435/6 |

\* cited by examiner

*Primary Examiner*—Bryan Bui
*Assistant Examiner*—Jonathan Teixeira Moffat
(74) *Attorney, Agent, or Firm*—Spencer Fane; Britt & Browne LLP (57) ABSTRACT

A method of classifying high-dimensional data to facilitate subsequent processing of the data. Generally characterized, the method includes determining a statistical distribution function for a first dataset; determining a statistical distribution function for a second dataset; identifying a characterizing feature of the first and second datasets; determining a probability of distinction based on the first and second statistical distribution functions, with the probability of distinction being the probability that the characterizing feature can be used to distinguish the first dataset from the second dataset; and identifying a subject of the first dataset based on the probability of distinction. Once the subject has been identified, the first dataset can be further analyzed using processing techniques appropriate to the subject.

13 Claims, 8 Drawing Sheets

|   | $x^1$ | ... | $x^k$ | $x^{k+1}$ | ... | $x^n$ | $p$ |
|---|---|---|---|---|---|---|---|
| $f_1$ | $x_{1,1}$ | ... | $x_{1,k}$ | $x_{1,k+1}$ | ... | $x_{1,n}$ | $p_1$ |
| $f_2$ | $x_{2,1}$ | ... | $x_{2,k}$ | $x_{2,k+1}$ | ... | $x_{2,n}$ | $p_2$ |
| ... | ... | ... | ... | ... | ... | ... | ... |
| $f_m$ | $x_{m,1}$ | ... | $x_{m,k}$ | $x_{m,k+1}$ | ... | $x_{m,n}$ | $p_m$ |
|   | 0 | ... | 0 | 1 | ... | 1 |   |

Table 1

FIG. 1

FeatureProb$(\alpha_0, N, C_i, T_i)$ 1. significance level $\alpha \leftarrow \alpha_0$
2. $\hat{\theta}_1 \leftarrow p$ - value K - S test on the control set $C_i$ and the treatment set $T_i$ at level $\alpha$
3. for $j = 2$ to $N$
4.   do generate bootstrap samples $C$ and $T$ from $C_i$ and $T_i$ respectively
5.   $\hat{\theta}_j \leftarrow p$ - value K - S test on $C$ and $T$
6. $\hat{\theta} \leftarrow (\hat{\theta}_1, \cdots, \hat{\theta}_N)$
7. return $\#(\hat{\theta} < \alpha)/N$

| m/z interval | $f_{(710,711)}$ | $f_{(8000,8001)}$ | $f_{(9054,9065)}$ |
|---|---|---|---|
| original p-value | 0.9579 | 5.1125e-9 | 0.0675 |
| bias | -1.9318e-14 | 0 | -3.0531e-16 |
| standard error | 1.9328e-14 | 0 | 3.0546e-16 |
| $Pr(t'_{r,r+1}|\alpha = 5\%)$ | 0.094 | 1 | 0.55 |
| $Pr(t'_{r,r+1}|\alpha = 1\%)$ | 0.029 | 1 | 0.318 |

| | Data reduced by Pr(/|a = 0.1%) = 1 | | | | Data reduced by Pr(/|a = 0.1%) > 0.9 | | | | Data reduced by Pr(/|a = 0.1%) > 0.6 | | | |
|---|---|---|---|---|---|---|---|---|---|---|---|---|
| | Control | | Cancer | | Control | | Cancer | | Control | | Cancer | |
| k | Mean | sd | Mean | sd | Mean | sd | Mean | sd | Mean | sd | Mean | sd |
| 2 | 0.9855 | 0.0081 | 0.9804 | 0.0094 | 0.9858 | 0.0072 | 0.9831 | 0.0112 | 0.9842 | 0.0069 | 0.9856 | 0.0084 |
| 3 | 0.9883 | 0.0092 | 0.9813 | 0.0092 | 0.9892 | 0.0070 | 0.9896 | 0.0071 | 0.9864 | 0.0092 | 0.9890 | 0.0072 |
| 4 | 0.9874 | 0.0081 | 0.9836 | 0.0110 | 0.9915 | 0.0072 | 0.9895 | 0.0078 | 0.9886 | 0.0085 | 0.9890 | 0.0070 |
| 5 | 0.9893 | 0.0088 | 0.9827 | 0.0093 | 0.9890 | 0.0104 | 0.9883 | 0.0076 | 0.9884 | 0.0079 | 0.9902 | 0.0076 |
| 6 | 0.9892 | 0.0101 | 0.9809 | 0.0099 | 0.9901 | 0.0079 | 0.9886 | 0.0080 | 0.9891 | 0.0092 | 0.9896 | 0.0078 |
| 7 | 0.9883 | 0.0104 | 0.9821 | 0.0100 | 0.9881 | 0.0099 | 0.9904 | 0.0080 | 0.9878 | 0.0104 | 0.9902 | 0.0093 |
| 8 | 0.9910 | 0.0081 | 0.9821 | 0.0110 | 0.9900 | 0.0096 | 0.9911 | 0.0086 | 0.9903 | 0.0071 | 0.9915 | 0.0061 |
| 9 | 0.9896 | 0.0095 | 0.9801 | 0.0111 | 0.9885 | 0.0134 | 0.9888 | 0.0075 | 0.9893 | 0.0092 | 0.9914 | 0.0083 |
| 10 | 0.9885 | 0.0111 | 0.9823 | 0.0105 | 0.9885 | 0.0123 | 0.9891 | 0.0088 | 0.9886 | 0.0118 | 0.9904 | 0.0074 |

FIG. 7

| | SIGNIFICANCE LEVEL α | | | |
|---|---|---|---|---|
| THRESHOLD | 0.1% | 0.5% | 1% | 5% |
| 1 | 1328 | 2015 | 2403 | 3542 |
| 0.9 | 4274 | 5111 | 5481 | 6556 |
| 0.7 | 5423 | 6260 | 6660 | 7844 |
| 0.5 | 6232 | 7062 | 7530 | 8949 |

| Method | 2-fold Cross Validation | | | | 10-fold Cross Validation | | | | Leave one Out | |
|---|---|---|---|---|---|---|---|---|---|---|
| | Control | | Cancer | | Control | | Cancer | | #(Misclassification) | |
| GPMLE | 0.9842 | 0.0069 | 0.9856 | 0.0084 | 0.9886 | 0.0118 | 0.9904 | 0.0074 | 1 | 1 |
| GPBayes | 0.9819 | 0.0062 | 0.9831 | 0.0082 | 0.9887 | 0.0107 | 0.9881 | 0.0063 | 1 | 2 |
| BNN | 0.9723 | 0.0090 | 0.9862 | 0.0101 | 0.9790 | 0.0122 | 0.9886 | 0.0085 | 2 | 2 |
| SVM | 0.9414 | 0.0214 | 0.8929 | 0.0177 | 0.9584 | 0.0189 | 0.9028 | 0.0271 | 4 | 13 |
| bagging of MLP | 0.9221 | 0.0180 | 0.9697 | 0.0134 | 0.9368 | 0.0156 | 0.9753 | 0.0149 | 6 | 2 |
| 1-NN | 0.8793 | 0.0299 | 0.8883 | 0.0223 | 0.9304 | 0.0137 | 0.8956 | 0.0118 | 6 | 13 |
| 2-NN | 0.8409 | 0.0377 | 0.8775 | 0.0280 | 0.8893 | 0.0216 | 0.9024 | 0.0210 | 9 | 7 |
| CART | 0.7836 | 0.0478 | 0.8225 | 0.0377 | 0.8439 | 0.0372 | 0.8730 | 0.0288 | 16 | 16 |
| GPMLE | 0.9842 | 0.0069 | 0.9856 | 0.0084 | 0.9886 | 0.0118 | 0.9904 | 0.0074 | 1 | 1 |
| GPBayes | 0.9819 | 0.0062 | 0.9831 | 0.0082 | 0.9887 | 0.0107 | 0.9881 | 0.0063 | 1 | 2 |
| BNN | 0.9723 | | 0.0090 | | 0.9862 | | 0.0101 | | 0.9790 0.0101 | 0.9790 |

FIG. 11

```
# Load the necessary libraries
library(stats);
library(boot);

# Set the significance levels
SigLevel <- c(0.001,0.005,0.01,0.05) # significance level
NumLevel <- length(SigLevel);

# Read the data
Table <- read.table("KernelMatrix");

# Process the raw data
Dim <- dim(Table)[1];
Sample <- Table;
# Sample <- Table[,2:dim(Table)[2]]; # Filter the m/z out, the "pure" data
NumSample <- dim(Sample)[2]; # The number of sample points NumCtl <- 95; # The number of controls
CtlLabel <- 1:NumCtl;
CanLabel <- (NumCtl+1):NumSample;

# Settings of KS-tests
NumBoot <- 1000; # The number of recursions
Out <- matrix(0,Dim,NumLevel); # Result matrix

# Definition of feature selection function
fs.p <- function(d,l){
    ks.test(t(d[1:NumCtl])[l],t(d[(NumCtl+1):NumSample])[l])$p.value;
}

# Bootstrapping the acceptance probability
for(s in 1:Dim){
    temp <- boot(as.matrix(Sample)[s,],fs.p,R=NumBoot,stype="i")$t; # the
    argument of t record the results of bootstrapping
    for(t in 1:NumLevel){
        Out[s,t] <- sum(temp<SigLevel[t]);
    }
    if(s %% 1000 == 0) write.table(Out,file="Prob4FS.ks",sep=" ");
    cat("The KS-tests on ",s,"-th feature have been finished.\n");
}

# The result of shallow feature selection
Out <- Out/NumBoot;
write.table(Out,file="Prob4FS.KernelMatrix",sep=" ");
```

FIG. 12

METHOD OF CLASSIFYING DATA USING SHALLOW FEATURE SELECTION

RELATED APPLICATIONS

The present U.S. non-provisional patent application claims priority benefit of an earlier-filed provisional patent application titled METHODS FOR ANALYZING DATA, Ser. No. 60/802,365, filed May 22, 2006. The identified earlier-filed application is hereby incorporated by reference into the present application.

FIELD OF THE INVENTION

The present invention relates generally to biostatistical methods of classifying data, and, more particularly, to a method of classifying high-dimensional data to facilitate subsequent processing of the data.

BACKGROUND OF THE INVENTION

Cancer, the abnormal and uncontrolled division of cells causing benign or malignant growth, is the second leading cause of death in the U.S., exceeded only by heart disease. The early detection, classification, and prognosis of cancer remains the best way to ensure patient survival and quality of life.

Many current techniques to predict and classify cancer use deoxyribonucleic acid (DNA) microarray data, and, in particular, gene expression data, which allows for testing large quantities of genetic material. Generally, using the data, cells can be analyzed, genetic information can be extracted, and phenotypes can be determined, i.e., the characteristics of an organism, as determined by its genes and the relationship of the genes to the environment.

Typically, DNA molecules are placed on a microarray and attached using probes. Each of these DNA molecules may include a complement, generally referred to as a target or messenger ribonucleic acid (mRNA), which is, generally speaking, the working copy of genes within cells. When testing a cell from an organism, the mRNA is added to the microarray where the mRNA "hybridizes" with the DNA to which it is a complement. Thus, some of the discrete spots will contain mRNA hybridized to DNA, while other spots will not. In some technologies, the cellular mRNA is reverse-transcribed onto complementary DNA (cDNA), which is a complementary copy of the mRNA. The cDNA is linearly amplified and is subsequently used to hybridize with the probes.

The marker attached to the mRNA is used to determine which spots contain mRNA hybridized to DNA. Typically, the markers are fluorescent molecules that fluoresce when exposed to laser light of an appropriate frequency and power. This fluorescence can be measured to determine the degree to which a gene has expressed. For example, a high fluorescence detected for a particular gene indicates that the gene is very active. Conversely, a low or no fluorescence for a gene indicates that the gene is inactive. Thus, by examining the fluorescence of the microarray, the degree of activity of the different genes can be determined.

Using current techniques, it is possible to determine gene function for tissues affected and unaffected by a disease. By comparing the two phenotypes, it can be determined which genes contribute to certain diseases and how they contribute. However, current techniques are limited. In particular, the detection and classification of gene expression data is based on only a few observations. In many cases, only a few underlying gene components account for much of the data variation. For example, only a few linear combinations of a subset of genes may account for nearly all of the response variation. Unfortunately, it is exceedingly difficult to determine which genes are members of the subset given the number of genes in the microarray and the small number of observations. As such, given the number of genes on a single microarray (usually is in the thousands), a relatively small number of observations cannot provide accurate statistical data.

SUMMARY OF THE INVENTION

The present invention provides a method of classifying high-dimensional data to facilitate subsequent processing of the data. In one embodiment, the method comprises the steps of determining a statistical, e.g., cumulative, distribution function for a first dataset; determining a statistical distribution function for a second dataset; identifying a characterizing feature of the first and second datasets; determining a probability of distinction based on the first and second statistical distribution functions, wherein the probability of distinction is the probability that the characterizing feature can be used to distinguish the first dataset from the second dataset; and identifying a subject of the first dataset based on the probability of distinction. Once the subject has been identified, the first dataset can be further analyzed using processing techniques appropriate to the subject.

The first and second datasets may include microarray data, in which case the characterizing feature may be an expression of a gene associated with a particular biological mechanism such as, e.g., cancer. Alternatively, the first and second datasets may include surface-enhanced laser desorption ionization-time of flight data, in which case the characterizing feature may be a mass-to-charge ratio. The method may further include the step of filtering the data to eliminate potential characterizing features which would have low probabilities of distinction. The filter used in filtering the data may be based at least in part on the nature of the data or on the recognition of patterns in the data.

The method may further include the steps of identifying a plurality of characterizing features; determining a probability of distinction for each of the characterizing features; and selecting whichever of the characterizing features has the highest probability of distinction.

The method may further include the step of using the probability of distinction to specify a distribution of hyperparameters in a hierarchical model such as, e.g., a Bayesian neural network or a Gaussian process model.

It will be appreciated by those with ordinary skill in the art that, among other advantages, the present invention allows for, when genes are the subject of the data, determining a probability of importance for each gene. This probability, combined with some basic biological knowledge, may provide a better understanding of the genes, and, therefore, may improve the detection, classification, and diagnosis of diseases such as cancer.

These and other features of the present invention are described in greater detail in the section titled DETAILED DESCRIPTION, below.

BRIEF DESCRIPTION OF THE DRAWINGS

The following drawings are included to further demonstrate and clarify certain aspects of the present invention and are not meant to be limiting.

DETAILED DESCRIPTION OF THE INVENTION

With reference to the accompanying figures, a method is herein described, shown, and otherwise disclosed in accordance with one or more preferred embodiments of the present invention.

In one respect, the present invention provides methods for classifying high-dimensional data, and in particular, microarray data or surface-enhanced laser desorption ionization-time of flights (SELDI-TOF) data. The methods may use a "shallow feature selection" (SFS) that assigns each feature a probability of being selected based on, for example, an empirical distribution of the data. A "feature", as used herein, refers to an attribute or characteristic of the data. For example, for data concerning tissue, a feature of the data may be a protein expression level of the tissue. A "probability of distinction", or simply a "probability", as used herein, refers to a probability of a selected feature being able to distinguish between data classes (e.g., a normal sample and a cancerous sample). Using these methods, the microarray data or SELDI-TOF data can be reduced to an applicable case for subsequent processing.

In another respect, the probability assigned to a given feature may be used to specify a distribution or distributions of hyperparameters in hierarchical models of, for example, Bayesian neural networks (BNN) or Gaussian process models. Neural networks, such as BNN models, can be used in the classification and regression of data due to their ability to model complex non-linear systems. Theoretically, neural networks can simulate any continuous function in a compact range. Neural networks can simulate a continuous function if the number of hidden units approaches infinity, where "hidden units", as used herein, refers to the connection units between an input layer and an output layer.

Shallow Feature Selection

A normalized training set, D, with n samples is equal to $$\{(x^u, t^u) | x^u \in \mathfrak{R}^m, t^u \in \{0,1\} \text{ and } \mu=1,2,\ldots n\} \qquad \text{Eq. 1}$$

where $t^u \in \{0,1\}$ are class labels and samples $x^u$ are recorded in column vectors. In some embodiments, feature selection may be based on pattern recognition. Additionally or alternatively, some characteristics of the dataset itself may be used to filter useless features, such as features that have the same distributions across two different classes.

Figure 1:
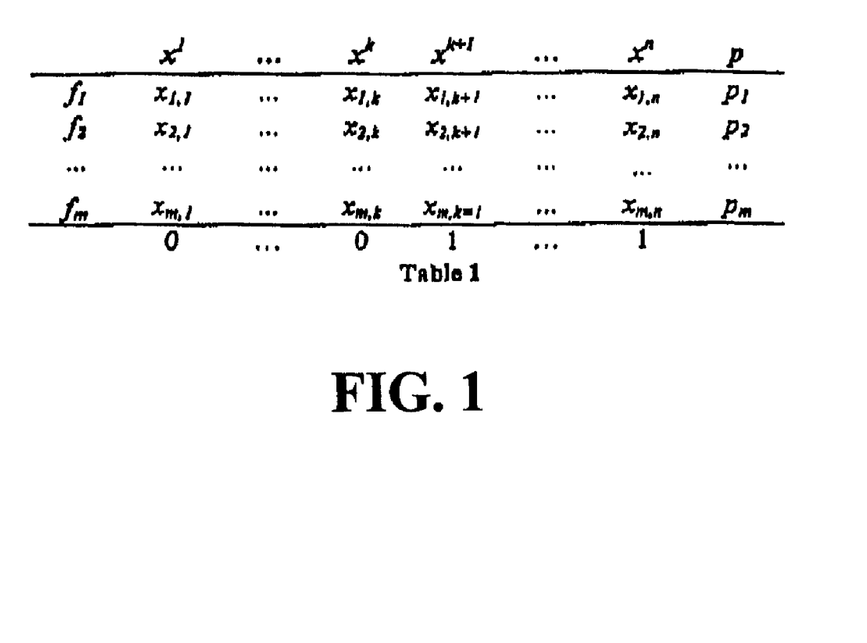
FIG. 1 is a table of features, associated samples, and associated probabilities of distinction.

For example, referring to FIG. 1, each sample, $x^i$, is denoted by a column vector, where $f_i$ represents a feature or attribute, e.g., the expression of a gene in microarray data or the mass-charge ratio in surface-enhanced laser desorption ionization-time of flight (SELDI-TOF) data, and $p_i$ is the probability a feature is selected. $f_i$ may be useful if the empirical distributions of the two datasets are statistically distinct. In other words, $f_i$ may be useful for two datasets with different data distributions. Moreover, for a reasonable representation of the training data, each feature in question may be associated with a prior probability of being selected for classification, independent of particular classifiers. These features, as used herein, refer to shallow feature selections (SFS).

Without any assumption of population distribution, the empirical distributions of values in $X_i=(x_{i,1}, \ldots, x_{i,k})$ and $X'_i=(x_{i,k+1}, \ldots, x_{i,n})$ may be compared using, for example, a two-sided Kolmogorov-Smirnov (KS) test (i.e., the null hypothesis $H_o$ where $X_i$ and $X'_i$ are drawn from the same continuous distribution) with a given level of significance, $\alpha$.

Due to the high dimensionality and relatively small amount of training data, the statistical difference between the control dataset $\{x_1, \ldots, x_c\}$ and the treatment dataset $\{x_{c+1}, \ldots x_n\}$ may be hard to survey. In one respect, $f_i$ should be assumed to be more important if the control dataset $\{C_i=\{x_{i,1}, \ldots, x_{i,c}\})$ and the training dataset $(T_i=\{x_{i,c+1}, \ldots, x_{i,n}\})$ are more probably from distinct populations.

Assuming $X_1, \ldots X_c^{iid} \sim F_1(z)$ and $Y_1, \ldots, Y_t^{iid} \sim F_2(z)$, the cumulative distribut function (CDF) $F_1(z)$ can be approximated by the empirical CDF $\hat{F}_1(z)$. By Gnedenko theorem, if $F_1(z)=F_2(z)$, the statistic of the $D_{c,t}=\sup|\hat{F}_1(z)-\hat{F}_2(z)|$ tends to be 0 c,t approaches infinity, $\infty$.

Moreover, Kolmogorov-Smirnov theorem affirms that $$\sqrt{\frac{ct}{n}} D_{c,t} \sim K(z)$$

where $$K(z) = 1 - 2\sum_{i=1}^{\infty} (-1)^{i-1} \exp(-2i^2 z^2)$$

is the CDF of Kolmogorov's distribution. Therefore, asymptotically, $D_{c,t}$ may serve as a test statistic for the null hypothesis $H_o: F_1(z)=F_2(z)$.

The strength of evidence against the null hypothesis $H_o$ is measured by a p-value defined by $\Pr(T>t_{obs}|H_o)$ where $t_{obs}$ is the value of a test statistic, T, for the observed data. In one respect, a smaller p-value is regarded as stronger evidence against $H_o$.

Figure 2:
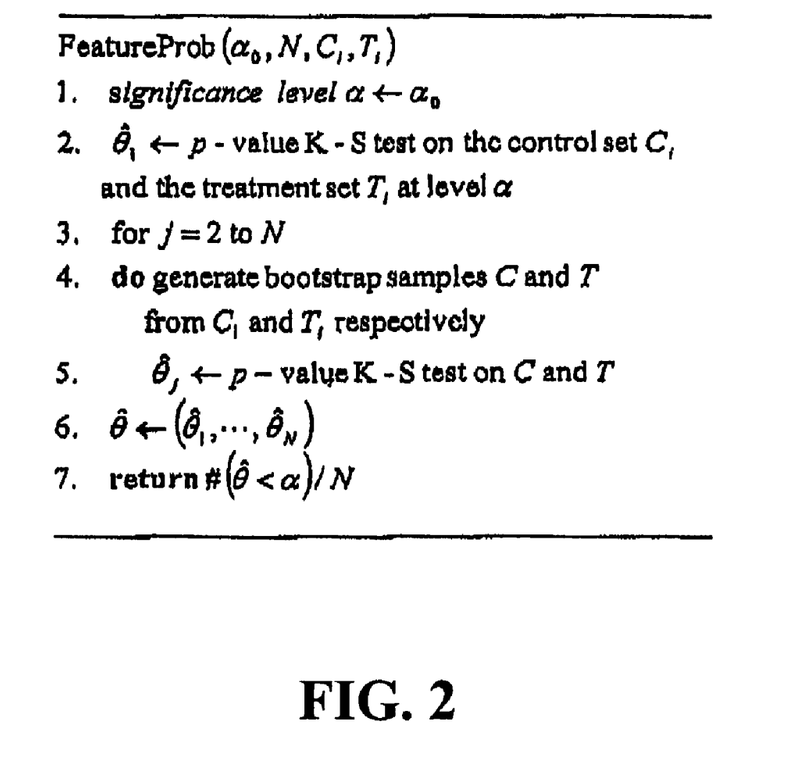
FIG. 2 is an exemplary algorithm of a bootstrap technique.

Referring to FIG. 2, an example algorithm based on the bootstrap technique of the present invention assigns a probability to $f_i$ based on the control dataset, $C_i$, and treatment dataset, $T_i$, denoted by $\Pr(f_i|a=a_o)$.

The bootstrap method requires no theoretical calculations no matter how mathematically complicated the estimator, $\hat{\theta}$. $\Pr(f_1|a_o)$ may be viewed as the degree of feature $f_i$ distinguishing the two datasets (e.g., control and training) at a precise-ness level of $\alpha_o$. In some embodiments, the SFS of the present invention provides users some prior knowledge of the importance of features for classification in view of the data structure itself. Furthermore, the empirical distribution of bootstrapping p-values $\hat{\theta}$ are able to show some statistical characteristics of the considered feature; for example, a small coefficient of variation is preferred.

After repeating the procedure (N−1) more times on the resampled training datasets, the simple voting will result in $Pr(f_i|a)=\#(H_o\text{rejected})/N$, the probability of choosing $f_i$ as a distinguishing feature at a level of confidence, $\alpha$.

Figure 3:
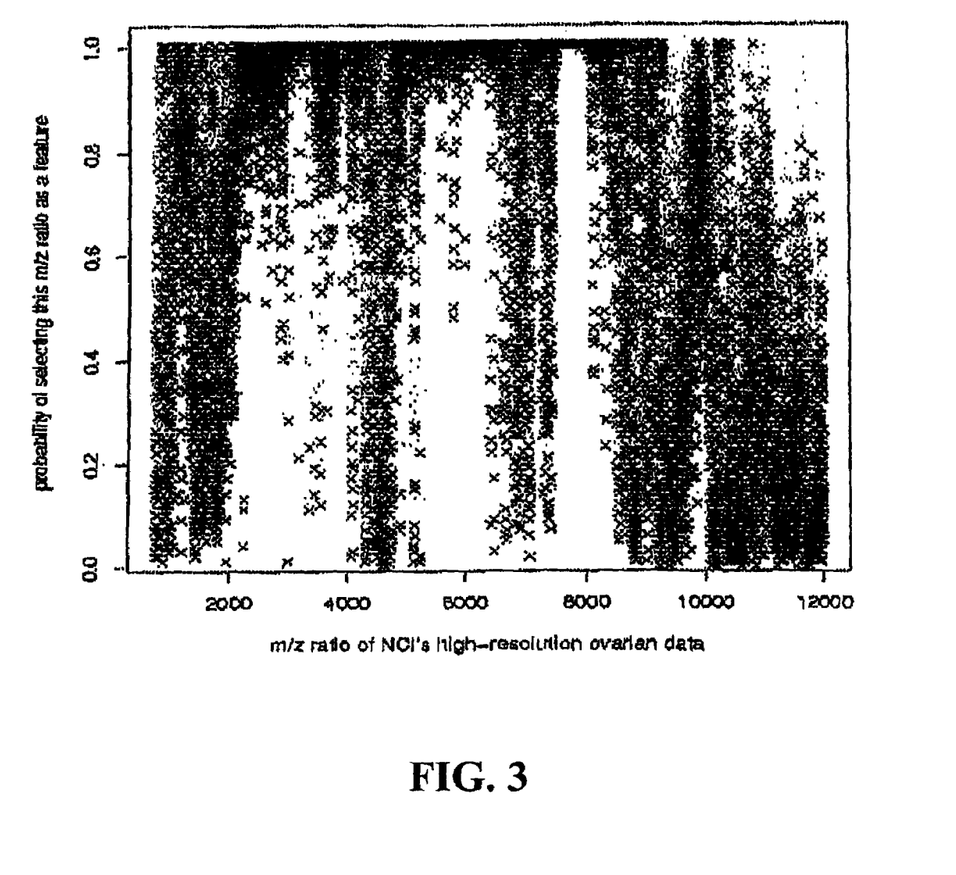
FIG. 3 is a scatter plot of probabilities of selecting an m/z ratio interval.

Referring to FIG. 3, a graph is shown illustrating the probability of selecting a certain feature. In this example, an ovarian dataset from the National Cancer Institute (NCI) was analyzed. For a particular mass-charge (m/z) ratio, a probability of selecting that ratio is determined. It is noted that while the NCI's dataset was used, in particular for the relevance of the data to cancer classification, other datasets may also be analyzed.

In some embodiments, feature selection may be based on the p-values guaranteed by $n_i n'_i/(n_i+n'_i) \geq 4$, where $n_i$, $n'_i$ are the sample sizes of $X_i$ and $X'_i$ repctively. Additionally, the bias and standard error calculated from the N bootstrap (a repeating step) replicates of the p-value may provide more information about SFS (see FIG. 4), especially for the amphibolous case of $Pr(f_i) \approx 0.05$, a standard confidence test level generally used in the art. Although the SFS is independent of specific classifiers, it may not isolate from classification. In BNN models, $Pr(f_i|)$ may be used to specify the covariance matrix of Gaussian processes and the prior distributions of input-to-hidden weights.

In contrast to some other classifier-independent approaches to data reduction, such as Principle Component Analysis (PCA), wavelet analysis, etc., SFS is capable of selecting a set of features without losing their biological meaning. In some embodiments, features with large discriminant power to distinguish two different datasets (e.g., a cancer dataset versus a normal dataset) may have a higher likelihood of being selected compared to features with small discriminant power. Furthermore, the probability assigned to each feature is actually a kind of prior knowledge about its contribution to classification, hence use of the term "prior probability" in this disclosure. In contrast, neither PCA nor wavelet utilizes class information in data reduction.

Binary Classifications of BNN

In contrast to conventional training methods for multilayer perceptron (MLP) that are based on maximum likelihood estimation, the Bayesian approach to neural networks utilizes the prior distribution of network weights before training and revises it after observing the data. Therefore, BNN can provide not only the means of predictive weights but also their uncertainties. Another advantage of BNN is the appropriate choices of a number of hidden layers and their dimensions, which are almost impossible to solve by traditional neural networks.

The inference of an underlying Bayesian binary classifier from D parameterized by the weight vector w, is to find $f(x,w|D,M)$ for the probability of x being in class 1 in model M. In some embodiments, M may be a logistic model where $f(x,w)=[1+\exp\{-h(x,w)\}]^{-1}$, satisfying $\int f(x,w)dx < \infty$ and where $h(x,w)$ is $$h(x, w) = \log \frac{Pr(t=1 \mid x, w)}{Pr(t=0 \mid x, w)} \qquad \text{Eq. 2}$$

Considering the approximation ability, h, is adopted to be the adaptive basis function of one hidden layer (with u units) perceptron $h(x,w)=b+W^T\psi(b+M^Tx)$. Since the biases b and b, if necessary, can be absorbed in $M^T$ and $W^T$, respectively, $h(x,w)$ may be considered as $$h(x,w)=W^T\psi(M^Tx)=W^Ty \qquad \text{Eq. 3}$$

where $w=(M,W)$ and $\psi$ is a bounded activation function, such as hyperbolic tangent $\tanh(z)=[\exp(-z)]/[\exp(z)+\exp(-z)]$, or error function $$\text{erf}(z) = \frac{2}{\sqrt{\pi}} \int_0^z \exp(-t^2) dt.$$

The binary classification is a noise-free regression problem of logit $(Pr(x \in \text{class } 1))=h(x,w)$, where $\text{logit}(p)=\log(p/1-p)$. As such, the likelihood is $$Pr(D \mid w) = \prod_{\mu=1}^{n} f(x^\mu, w)^{t^\mu}(1 - f(x^\mu, w))^{1-t^\mu} \qquad \text{Eq. 4}$$

Once given p(w), the posterior distribution of parameters p(w|D) (proportional to p(w)p(D|w)) may be clear, and the probability of testing sample x being in class 1 is $$Pr(t_{new} = 1 \mid x_{new}, D) = \int f(x_{new}, w)p(w \mid D)dw \qquad \text{Eq. 5}$$

$$\approx \frac{1}{N} \sum_{i=1}^{N} f(x_{new}, w_i)$$

where $w_i$ are drawn from a population of p(w|D). The intuitive assumption of $p(w) \sim \exp\{-\xi w^T w/2\}$ relies on the belief that smaller weights lead to less certain predictions, where the hyperparameter $\xi$ is defined in a hierarchical model, for example, the automatic relevance determination. The integral in Eq. 5 can be evaluated using, for example, a Metropolis algorithm.

Again, the desired p(w) may be viewed as the prior distribution over all the functions described by Eq. 3. Motivated by the Gaussian process (GP) approach to nonparametric Bayesian regression, a large class of neural network models converge to Gaussian processes in the limit of an infinite number of hidden units, and the overfitting problem may be alleviated by some hierarchical model of hyperparameters. Theoretically, finite-dimensional distributions of GP may be determined by its finite mean and covariance functions.

Figure 5:
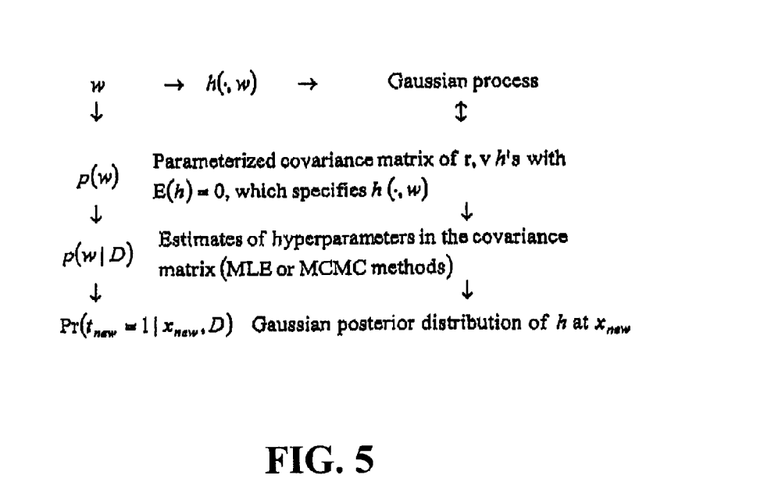
FIG. 5 is a comparison between a traditional method and a Gaussian process method.

An advantage of using a GP approach is that there is no need to make complicated assumptions on the distribution of w. For a covariance function, however, a distribution of $h(x_{new}, w|D)$ may be achieved. Referring to FIG. 5, a comparison between a traditional method and the present GP method is shown.

Although the logistic model, in terms of latent values $h=h(x,w)$, may be specified by a wide variety of covariance functions, mainly it is in the form of $$\text{Cov}(h,h')=\delta_{hh'}\epsilon+c^2+x^T \text{diag}(\gamma_1^2, \ldots, \gamma_m^2)x'+\beta^2 \exp\{-(x-x')^T \text{diag}(\lambda_1^2, \ldots, \lambda_m^2)(x-x')\} \qquad \text{Eq. 6}$$

where $c^2, \gamma_i^2, \beta^2, \lambda_i^2$ are hyperparameters. Due to the computational issue, the covariance function often adds a "jitter" of $\delta_{hh'}\epsilon$ where $\epsilon > 0$ and $\delta_{hh'}$ is known as the Kronecker delta term of $c^2+x^T\text{diag}(\gamma_1^2,\ldots\lambda_m^2)x'$ is for the linear regression, where the last term is based on the assumption that nearby inputs will have highly correlated outputs, allowing a different distance measure for each input dimension than the smaller $\lambda_1^2$, which is less important of $i^{th}$ features.

The joint distribution of GP $h_{n+1}=(h^1,\ldots,h^n,h_{new})^T$ given $X_{n+1}=(x^1,\ldots$ and the parameterized covariance function matrix $K_{n+i}$ is $$h_{n+1}|X_{n+1},K_{n+1} \sim N_{n+1}(Eh_{n+1},K_{n+1}) \qquad \text{Eq. 7}$$

where $$K_{n+1} = \begin{pmatrix} K_n & K_{new} \\ k_{new}^T & k \end{pmatrix},$$

$$K_n = (\text{Cov}(h^\mu, h^\nu))_{m\times n},$$

$$k_{new} = (\text{Cov}(h^1, h_{new}), \ldots, \text{Cov}(h^n, h_{new}))^T$$

and $$k = \text{Cov}(h_{new}, h_{new})^T.$$

With the assumption of $Eh=0$ for the equal prior probability of each class, the conditional distribution of $h_{new}$ with hyperparameters gives $t_n=(t^1,\ldots,t^n)$ or equivalently $h_n=(h^1,\ldots,h^n)^T$, and $$h_{new}|x_{new},D,K_{n+1} \sim N(k_{new}^T K_n^{-1} h_n, k - k_{new}^T K_n^{-1} k_{new}) \qquad \text{Eq. 8}$$

For any hyperparameter in $\theta$ in $K_n$, it can be replaced by the maximum likelihood estimate (MLE) from $\partial L/\partial \theta = 0$, where $L$ is the log-likelihood of $h_n$ and is expressed as $$L = -\frac{n}{2}\log(2\pi) - \frac{1}{2}\log \det K_n - \frac{1}{2}h_n^t K_n^{-1} h_n \qquad \text{Eq. 9}$$

$$\frac{\partial L}{\partial \theta} = -\frac{1}{2}tr\left(K_n^{-1}\frac{\partial K_n}{\partial \theta}\right) + \frac{1}{2}h_n^T K_n^{-1}\frac{\partial K_n}{\partial \theta}K_n^{-1} h_n \qquad \text{Eq. 10}$$

Figure 6:
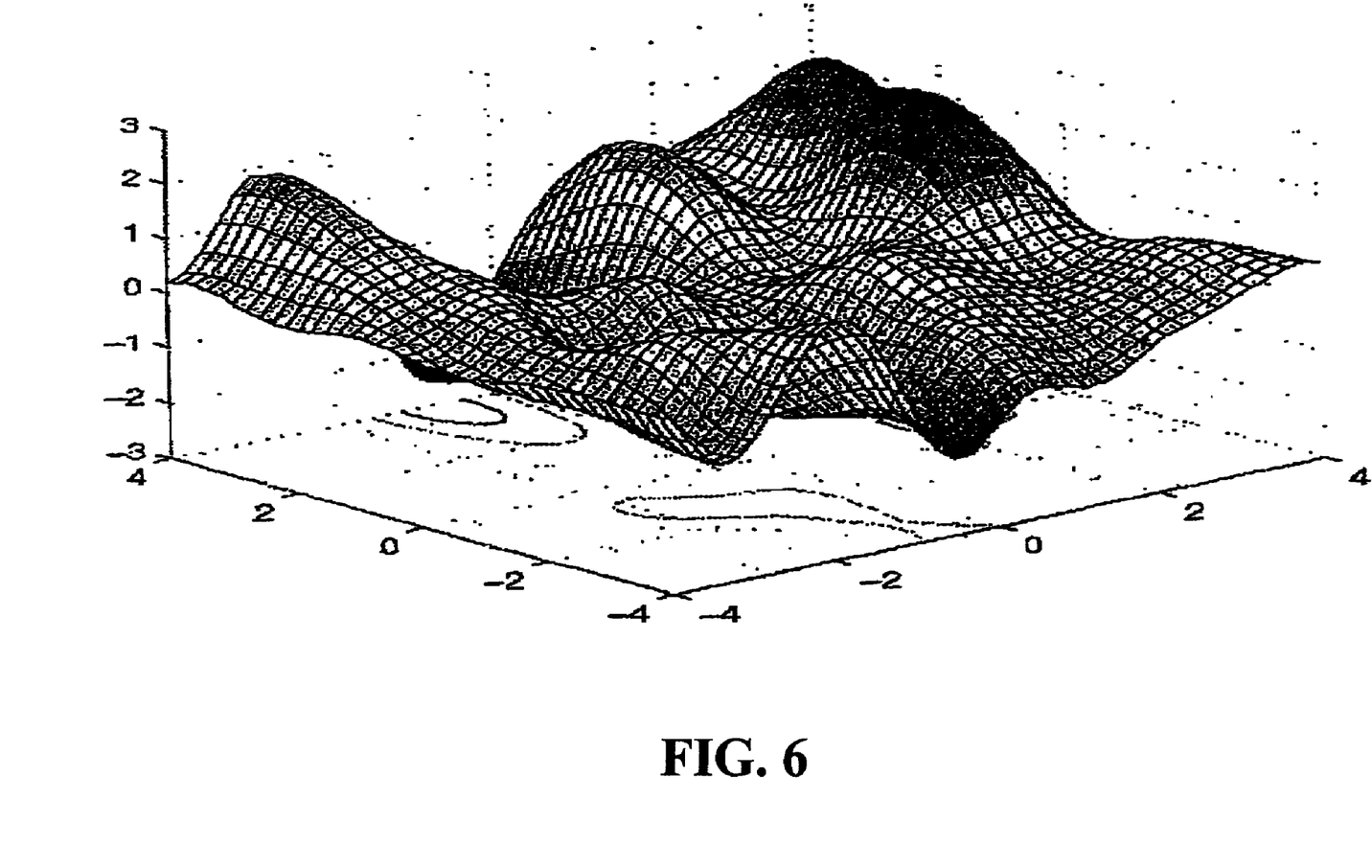
FIG. 6 is a plot of an h-surface generated network with a 2-dimensional input, in accordance with embodiments of the disclosure.

Referring to FIG. 6, a simulation of random h-surface for MLP with a 2-dimensional input generated by the MLE-based GP method is shown. The z-axis is the h-surface of a randomly generated network with a 2D input $(x_1,x_2)^T$, using Eq. 6, the x-axis is $x_1$ and the y-axis is $x_2$.

Referring again to Eq. 6, letting $y_i$ be the $i^{th}$ component of $y=\psi(M^T x)$, and $W \sim N_u(0, \sigma_0^2 I_u)$ and $Eh=0$ the covariance function for Eq. 3 is $$\text{Cov}(h, h') = \sigma_0^2 \sum_{i=1}^{u} E(y_i y_i') = u\sigma_0^2 E(y_u y_u'). \qquad \text{Eq. 11}$$

Assuming that $M_{\cdot,1},\ldots,M_{\cdot,u} \overset{iid}{\sim} N_m(0,\Sigma)$, where $\Sigma=\text{diag}(\sigma_1^2,\ldots,\sigma_m^2)$, the analytic covariance functions for both error and Gaussian transfers coincide with Eq. 6 under some conditions, such as when the variance is larger than the largest distance in x-space.

In some embodiments, parameter tuning may not be necessary for BNN models because of the hidden noisy features in high-dimensional data. Instead of being initialized randomly or trained under strong assumption of distributions, the MLE-based GP model is specified by $\lambda_i^2 = \gamma_i^2 = \Pr(f_i|\alpha)$, $\beta^2 = c^2 = 1$, $\epsilon = 0.001$ where $\Pr(f|\alpha)$ weakens the influence of "useless" features in the covariance function. This strategy may simplify the GP model and yields an excellent performance on specific gene data, as reflected in the ovarian data analysis shown in FIG. 7, where k is the matrix, mean is the mean value, SD is the standard deviation, control is a normal sample and cancer is a diseased sample.

In some embodiments, feature selection may be suitable for all classifiers because the categorical characteristics explored and utilized by distinct methods could be quite different Alternatively, for a BMM, each parameter may be estimated as the mean of its posterior distribution using, for example, Markov Chain Monte Carlo (MCM) methods. The following will specify the distributions for mutually independent parameters in a BNN model and a GP model, respectively. These two fully Bayesian methods, together with the MLE method for the GP model, will be examined on the National Cancer Institute's (NCI) ovarian data described in detail below.

In one embodiment, a mathematically convenient prior of unknown variance is an inverse gamma distribution, the conjugate family for Gaussian weights. In one respect, the conjugate family for Gaussian weights are:

$$W|\sigma_0^2 \sim N_u(0, \sigma_0^2 I_u) \qquad \text{Eq. 12}$$

$$\sigma_0^2 \sim \text{Inv-Gamma}(a_0, b_0) \qquad \text{Eq. 13}$$

$$M_{\cdot,i}|\Sigma \sim N_m(0,\Sigma) \qquad \text{Eq. 14}$$

$$\sigma_i^2 \sim \text{Inv-Gamma}(a_i, b_i) \qquad \text{Eq. 15}$$

where Inv-Gamma $$(\theta \mid a, b) = \frac{b^a}{\Gamma(a)}\theta^{-(a+1)}\exp(-b/\theta), \theta > 0 \text{ with shape } a < 0$$

and scale $b > 0$.

The full conditionals of $\sigma_0^2$ and $\sigma_i^2$ are $$\sigma_0^2|W,M,\Sigma,D \sim \text{Inv-Gamma}(a_0+u/2, b_0+\|W\|^2/2) \qquad \text{Eq. 16}$$

$$\sigma_i^2|\sigma_0^2,\ldots,\sigma_{i-1}^2,\sigma_{i+1}^2,\ldots,\sigma_m^2,W,M,D \sim \text{Inv-Gamma}(a_i+u/2, b_i+\|M_{i\cdot}\|^2/2) \qquad \text{Eq. 17}$$

where $a_0=0.01, b_0=0.5, a_i=0.01, b_i=\Pr(f_i|a)$ to make the density flatter for larger $\Pr(f|a)$.

In a fully Bayesian model of GP, the prior probability of linear part $\gamma^2=(\gamma_1^2,\ldots,\gamma_m^2)^T$ and relevance $\lambda^2=(\lambda_1^2,\ldots,\lambda_m^2)^T$ are similar to that of $M_j$ (Eq. 14), and the prior probability of scale $\beta^2$ is similar to that of $W_i$ (Eq. 12). The jitter $\epsilon$ and constant c shown in Eq. 6 are set to be 0.01 and 1 respectively.

Experiments and Analysis

Figure 4:
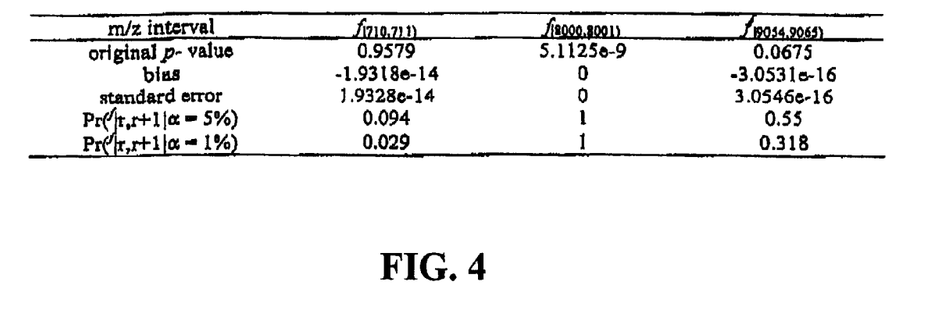
FIG. 4 is a table of bootstrapped p-values for SFS of m/z intervals.
Figure 8:
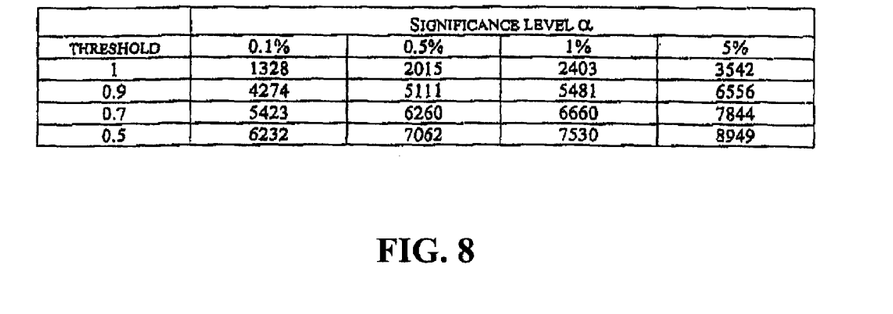
FIG. 8 is a table of features at various significance levels and thresholds.

For each k-fold cross validation of an embodiment of the MLE-based GP method ($k=2,\ldots,10$), independent experiments have been repeated 1,000 times on the reduced data by SFS to get the average specificity and sensitivity with a corresponding standard deviation (see FIG. 4). The number of selected features may be controlled by both $\alpha$ and the threshold, for instance on the original binned data, as shown in FIG. 8.

Figure 7:
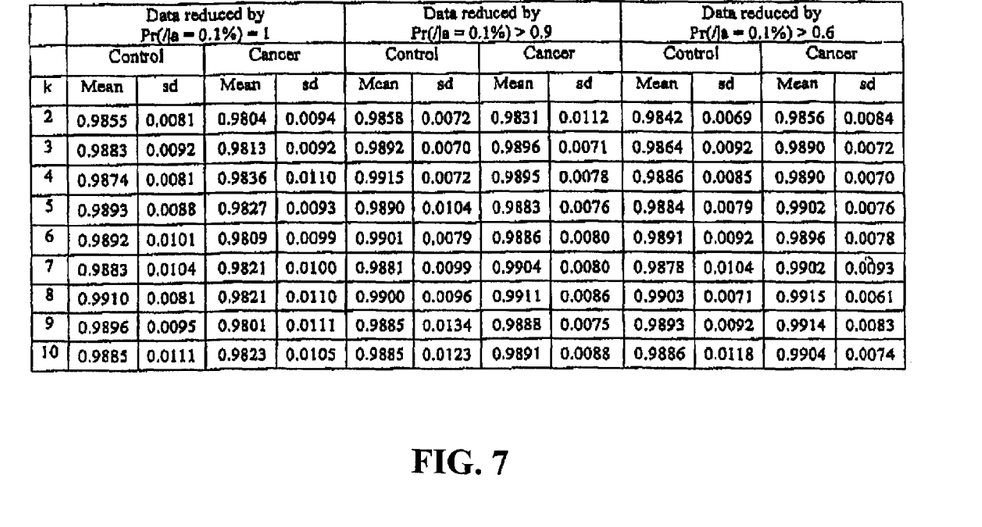
FIG. 7 is a table of analyzed ovarian cancer data.

Similarly, MLE-based GP model (GPMLE) generally behaves very stably in leave-one-out cross validations on distinct reduced datasets (see the last row of FIG. 7).

Figure 9:
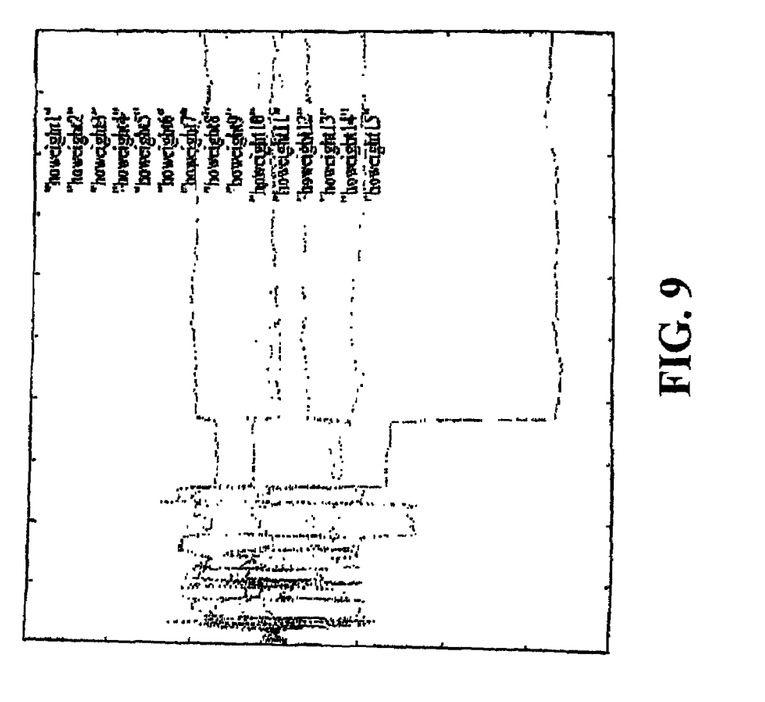
FIG. 9 is a plot of a simulation of hidden-to-output weights.
Figure 10:
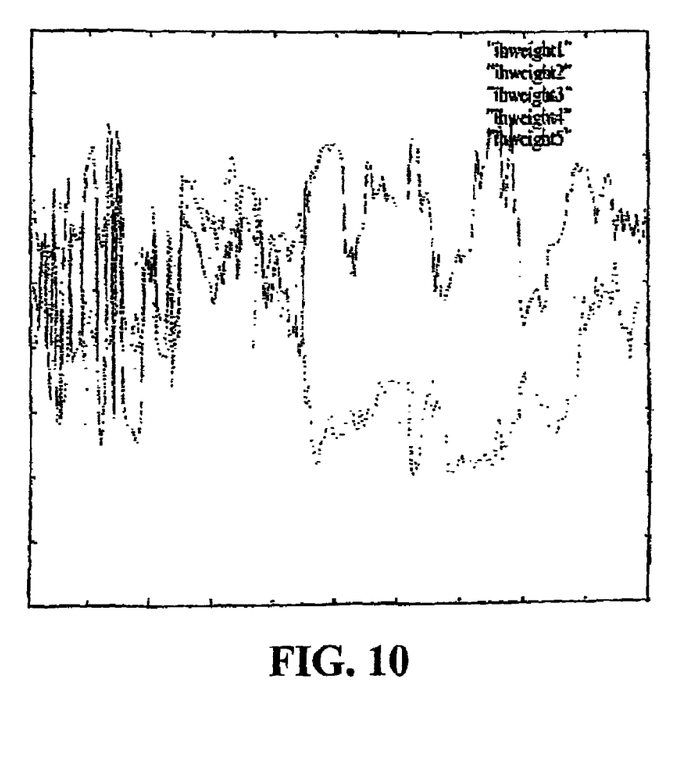
FIG. 10 is a plot of a simulation of five input-to-hidden weights.

In one embodiment, a Hybrid Monte Carlo (HMC) method may be used to compute tractable Bayesian integrals by using dynamical methods and Metropolis acceptance rules to propose and accept transition states. In one respect, an NN with one hidden layer of 15 units, where the hidden-to-output weights converge after 80 iterations was analyzed, as shown in FIGS. 9 and 10. In FIG. 9, the left figure is the HMC simulation of hidden-to-output weights, where u=15 and the z-axis is the number of iterations; in FIG. 10, the simulation of the first five input-to-hidden weights of hidden unit 1 are shown. Comparing the GP$_{MLE}$ and SVM, the fully Bayesian methods are both accurate and efficient.

Figure 11:
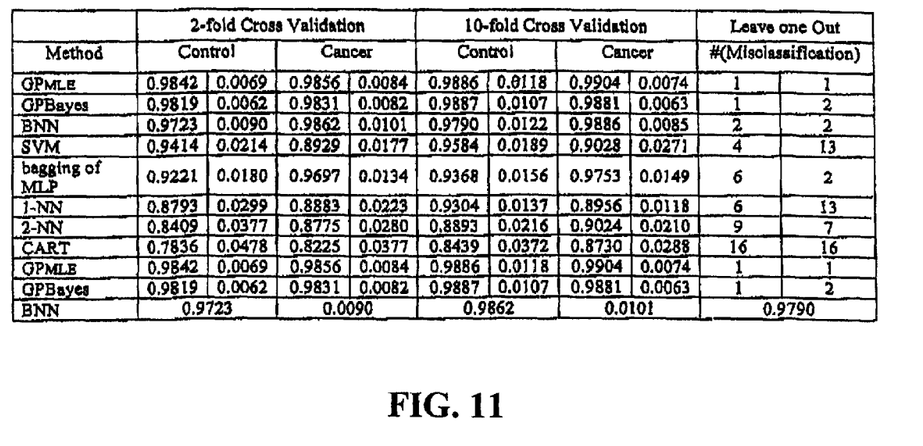
FIG. 11 is a table comparing various classifier methods.

Although other classifiers may be used, others that were tested were found to be inferior to those by BNN (see FIG. 11). Some sophisticated techniques of data reduction, such as, but not limited to, restriction of coefficient of variation, wavelet analysis, or SVM with soft margin, may also provide good performance of sensitivity and specificity on NCI's ovarian data. Regardless of the computational complexity, the bagging of MLP is able to yield another reliable Pr($t_{new}|x_{new}$,D), especially for the small training sample, from the viewpoint of ensemble learning. Several samples were found almost always misclassified in cross validations; for example, those explored by MLP bagging in FIG. 11.

Figure 12:
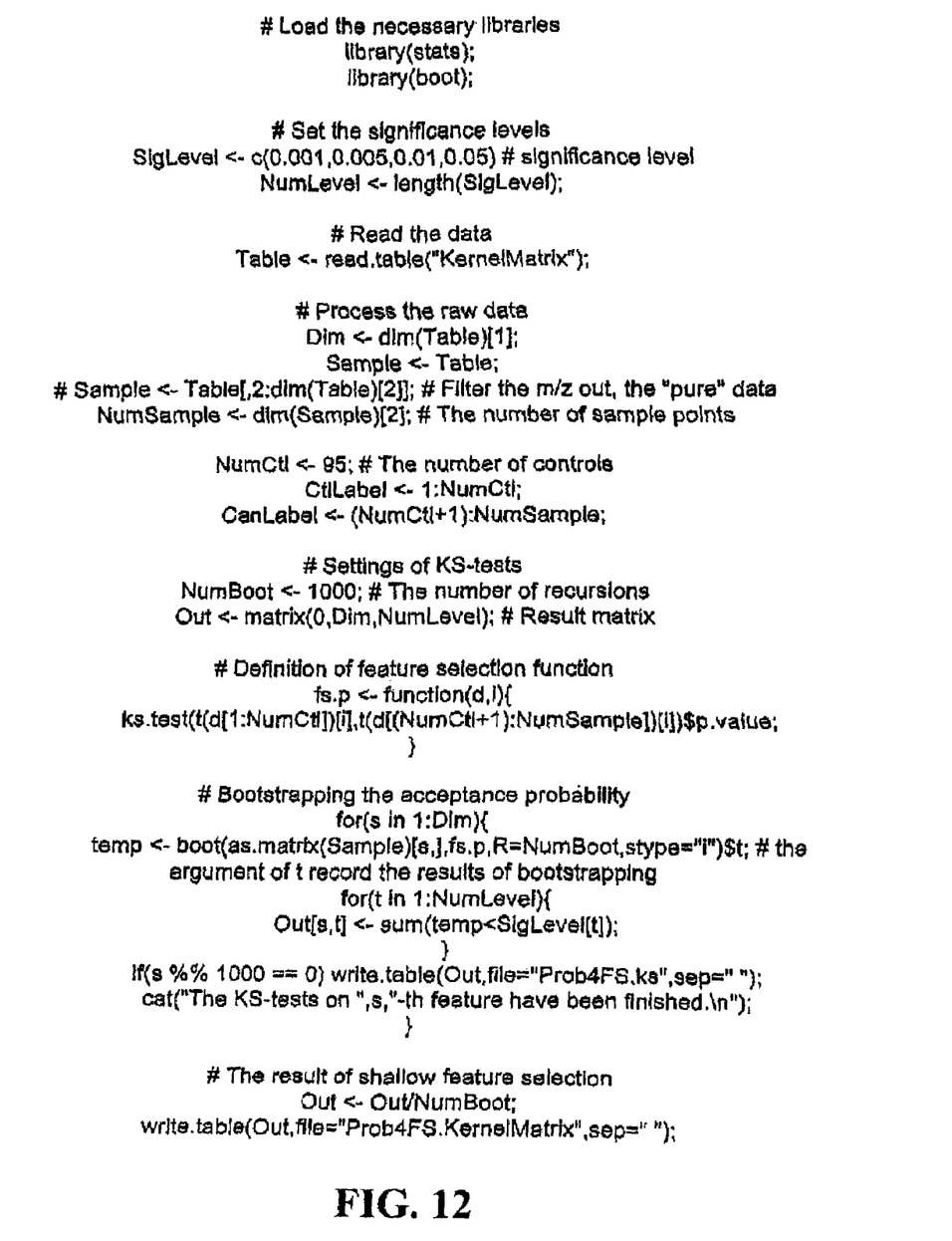
FIG. 12 is a listing of source code for implementing a method for analyzing data.

Features of the present disclosure may be substantially automated, i.e., computerized. An exemplary computer code for implementing all or parts of this disclosure is shown in FIG. 12. The code may be stored in or on any suitable computer readable media, and may be accessed and executed by any suitable computing device, such as a personal desktop or portable computer.

Although the invention has been disclosed with reference to various particular embodiments, it is understood that equivalents may be employed and substitutions made herein without departing from the scope of the invention as recited in the claims.

What is claimed is:

1. A computer program product comprising code stored on a tangible computer-readable medium which, when operated on by a computer, performs a method of classifying high-dimensional data to facilitate subsequent processing of the data, the method comprising:
   determining a first cumulative distribution function for a feature of a first dataset, wherein the first data set represents a first class;
   determining a second cumulative distribution function for the feature of a second dataset, wherein the second data set represents a second class;
   determining a probability of distinction of the feature based on a difference between the first and second cumulative distribution functions, wherein the probability of distinction is the probability that the feature can be used to accurately classify test data as belonging to one of the first and second classes;
   using the feature to assign the test data to one of the first and second classes;
   using the probability of distinction to specify a distribution of hyperparameters in a hierarchical model; and
   using the hierarchical model to assign the test data to one of the first and second classes.

2. The method as set forth in claim 1, wherein the first and second datasets include microarray data.

3. The method as set forth in claim 2, wherein the feature is an expression of a gene associated with a particular biological mechanism.

4. The method as set forth in claim 3, wherein the biological mechanism is cancer.

5. The method as set forth in claim 1, wherein the first and second datasets include surface-enhanced laser desorption ionization-time of flight data.

6. The method as set forth in claim 5, wherein the feature is a mass-to-charge ratio.

7. The method as set forth in claim 1, further including the step of filtering the first and second data sets to eliminate potential features which would have low probabilities of distinction.

8. The method as set forth in claim 7, wherein filtering the first and second data sets uses a filter based at least in part on the nature of the data.

9. The method as set forth in claim 7, wherein filtering the first and second data sets uses a filter based at least in part on the recognition of patterns in the data.

10. The method as set forth in claim 1, further including the steps of identifying a second feature of the first and second data sets;
    determining a second probability of distinction for the second feature; and
    using whichever of the first and second features has the highest probability of distinction to assign the test data to one of the first and second classes.

11. The method as set forth in claim 1, wherein the hierarchical model is a Beyesian neural network.

12. The method as set forth in claim 1, wherein the hierarchical model is a Gaussian process model.

13. A computer program product comprising code stored on a tangible computer-readable medium which, when operated on by a computer, performs a method of classifying data to facilitate processing of the data, the method comprising the steps of:
    (a) randomly selecting a first plurality of samples from a first data set and a second plurality of samples from a second data set, wherein the first data set represents a first class and the second data set represents a second class, and wherein the members of the first and second data sets have one or more original features in common;
    (b) determining, for each of the one or more original features, a first cumulative distribution function of Kolmogorov's distribution of the first plurality of samples;
    (c) determining, for each of the one or more original features, a second cumulative distribution function of Kolmogorov's distribution of the second plurality of samples; and
    (d) repeating steps (a) through (c) a predetermined number of times;
    (e) determining, for each of the one or more original features, a probability of importance based on a statistical difference between the first and second cumulative distribution functions,
    (f) selecting at least one original feature of the one or more original features based on its probability of importance;
    (g) identifying a classifier based on the first and second data sets, the selected at least one feature, and the probability of importance for the selected at least one feature; and
    (h) using the classifier to assign test data to either the first class or the second class.

* * * * *